United States Patent
Nishikawa

(10) Patent No.: US 8,933,696 B2
(45) Date of Patent: Jan. 13, 2015

(54) MAGNETIC SENSOR AND BIOMAGNETISM MEASUREMENT SYSTEM

(75) Inventor: Takuo Nishikawa, Fussa (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 14/114,972

(22) PCT Filed: May 16, 2012

(86) PCT No.: PCT/JP2012/062452
§ 371 (c)(1),
(2), (4) Date: Oct. 31, 2013

(87) PCT Pub. No.: WO2012/161037
PCT Pub. Date: Nov. 29, 2012

(65) Prior Publication Data
US 2014/0062472 A1    Mar. 6, 2014

(30) Foreign Application Priority Data

May 20, 2011 (JP) ................................. 2011-113055
Jun. 2, 2011 (JP) ................................. 2011-123990

(51) Int. Cl.
*G01R 33/09* (2006.01)
*A61B 5/04* (2006.01)
(Continued)

(52) U.S. Cl.
CPC .......... *G01R 33/093* (2013.01); *A61B 5/04008* (2013.01); *A61B 5/6803* (2013.01);
(Continued)

(58) Field of Classification Search
CPC ................. A61B 2562/0223; A61B 2562/046; A61B 5/6803; A61B 5/04005; A61B 5/04008; G01R 33/098; G01R 33/093
USPC ........... 324/248, 249, 252; 600/409, 544, 545
See application file for complete search history.

(56) References Cited

U.S. PATENT DOCUMENTS

2004/0257186 A1 * 12/2004 Kaiju et al. .................... 335/296
2013/0099780 A1 * 4/2013 Ma et al. ....................... 324/249
(Continued)

FOREIGN PATENT DOCUMENTS

JP          02-040578 A     2/1990
JP          03-001839 A     1/1991
(Continued)

OTHER PUBLICATIONS

International Preliminary Report on Patentability and Written Opinion in Japanese and English. Date of Issuance: Nov. 20, 2013 (10 pages).
(Continued)

*Primary Examiner* — Huy Q Phan
*Assistant Examiner* — Adam Clarke
(74) *Attorney, Agent, or Firm* — Lucas & Mercanti, LLP

(57) ABSTRACT

A magnetic sensor includes a plurality of assemblies combined. Each assembly includes a plurality of tunnel magnetoresistive elements, a capacitor and a fixed resistor. The tunnel magnetoresistive elements are (i) disposed in such a way that fixed magnetization directions of fixed magnetic layers are substantially identical and changeable magnetization directions of free magnetic layers with no magnetic field applied are substantially identical and (ii) connected to each other in series-parallel. The capacitor is connected in parallel to the tunnel magnetoresistive elements. The fixed resistor is connected in series to the tunnel magnetoresistive elements and to the capacitor. The assemblies are (i) disposed in such a way that the fixed magnetization directions of the fixed magnetic layers of the assemblies have a relative angle of more than 90 degrees and (ii) connected to each other in series and/or in parallel.

10 Claims, 19 Drawing Sheets

(51) Int. Cl.
   *A61B 5/00*    (2006.01)
   *H01F 10/32*   (2006.01)
(52) U.S. Cl.
   CPC ........... *G01R33/098* (2013.01); *A61B 5/04005* (2013.01); *A61B 2562/0223* (2013.01); *A61B 2562/046* (2013.01); *H01F 10/3254* (2013.01)
   USPC ........... 324/249; 324/248; 324/252; 600/409; 600/544; 600/545

(56) References Cited

U.S. PATENT DOCUMENTS

| | | | |
|---|---|---|---|
| 2013/0249545 A1* | 9/2013 | Horsley et al. | 324/252 |
| 2013/0324832 A1* | 12/2013 | Wu et al. | 600/409 |

FOREIGN PATENT DOCUMENTS

| | | |
|---|---|---|
| JP | 2000-193364 A | 7/2000 |
| JP | 2004-065605 A | 3/2004 |
| JP | 2007-017248 A | 1/2007 |
| JP | 2007-24598 A | 2/2007 |
| JP | 2007-108083 A | 4/2007 |
| JP | 2009-52963 A | 3/2009 |
| JP | 2009-125396 A | 6/2009 |
| JP | 2010-148578 A | 7/2010 |
| JP | 2010-151508 A | 7/2010 |

OTHER PUBLICATIONS

International Search Report of PCT/JP2012/062452 dated Aug. 7, 2012.

P. Gomez et al; A Method to Design High SNR Nanoscale Magnetic Sensors Using an Array of Tunnelling Magneto-Resistance (TMR) Devices; J. Phys. D; Appl. Phys. vol. 40, 2007, pp. 4396-4404.

S. Yokota et al; Tunnel Magnetoresistance and Noise in Magnetic Tunnel Junction Array; Japan Society of Applied Physics; 2010, 14p-J-6.

* cited by examiner

MAGNETIC SENSOR AND BIOMAGNETISM MEASUREMENT SYSTEM

CROSS REFERENCE TO RELATED APPLICATION

This Application is a 371 of PCT/JP2012/062452 filed on May 16, 2012, which claims the priority of Japanese Patent Application No. 2011-113055 filed on May 20, 2011 and Japanese Patent Application No. 2011-123990 filed on Jun. 2, 2011, each of which are incorporated herein by reference in their entirety.

FIELD OF THE INVENTION

The present invention relates to a magnetic sensor and a biomagnetism measurement system.

BACKGROUND OF THE ART

As a device to measure magnetism emitted from a living body, a biomagnetism measurement device using SQUID (Superconducting Quantum Interference Device) sensors has been researched (Patent Documents 1 to 5, for example). By arranging a large number of SQUID sensors and using the SQUID sensors to measure biomagnetism, two-dimensional magnetism information such as magnetoencephalograms or magnetocardiograms can be obtained.

In order to measure biomagnetism with SQUID sensors, the SQUID sensors need to be maintained in a superconductive state with a refrigerant. Hence, SQUID sensors are placed in a Dewar flask where a refrigerant is stored and are used for the measurement in a state in which the SQUID sensors are soaked in the refrigerant.

There has been proposed a biomagnetism measurement device in which a portion of the outer wall part of a refrigerant tank of a Dewar flask is formed in a shape fit for a measurement target part of a living body such as a skull and many SQUID sensors are arranged on the inner side of the outer wall part in such a way as to be soaked in a refrigerant. The biomagnetism measurement device can obtain a magnetoencephalogram or the like by touching a living body with the outer side of the outer wall part and accordingly bringing the many SQUID sensors close to the living body with a certain distance therebetween and by performing the measurement.

By the way, in order to detect weak biomagnetic signals, it is necessary to remove a large external magnetic field(s) and detect the signals.

While the signal strength of biomagnetic signals is $10^{-10}$ T order to $10^{-15}$ T order, large external magnetic fields (coarse magnetic fields) are very strong; for example, magnetic noise in a city is $10^{-7}$ T order and geomagnetism is $10^{-5}$ T order. If biomagnetic signals derived from a living body and a coarse magnetic field are sensed at the same time, the signals derived from a living body are drowned out by the coarse magnetic field.

Hence, in order to perform the measurement in an environment where no coarse magnetic field exists, a magnetism shielded room or the like is proposed.

Further, in order to remove external magnetic fields, a gradiometer is proposed for a biomagnetism detection device using SQUID, for example.

The gradiometer has two pickup coils arranged with a space therebetween and is described, for example, in Patent Documents 6 to 8.

Although the magnetism shielded room can shield large external magnetic fields (coarse magnetic fields), as with a magnetic field emitted from a heart being noise in neuromagnetic field measurement, a magnetic field emitted from a living body could be noise for biomagnetic signals of a detection target. Thus, the magnetism shielded room may be an insufficient measure.

RELATED ART DOCUMENT

Patent Document

Patent Document 1: Japanese Patent Application Laid-Open Publication No. hei 2-40578
Patent Document 2: Japanese Patent Application Laid-Open Publication No. hei 3-1839
Patent Document 3: Japanese Patent Application Laid-Open Publication No. 2000-193364
Patent Document 4: Japanese Patent Application Laid-Open Publication No. 2004-65605
Patent Document 5: Japanese Patent Application Laid-Open Publication No. 2007-17248
Patent Document 6: Japanese Patent Application Laid-Open Publication No. 2009-125396
Patent Document 7: Japanese Patent Application Laid-Open Publication No. 2010-148578
Patent Document 8: Japanese Patent Application Laid-Open Publication No. 2010-151508

SUMMARY OF THE INVENTION

The Problems to be Solved by the Invention

The biomagnetism measurement device using SQUID sensors has some problems which are difficult to be solved: for example, a refrigerant to keep the sensors at a low temperature is needed, and hence the biomagnetism measurement device increases in size; the sensors need to be arranged to be close to and flexible to fit a target part; and the sensors need to be arranged at high density.

Then, the inventor of the present invention thinks of using tunnel magnetoresistive (TMR) elements to measure biomagnetism as sensor devices which can be used at room temperature, contribute to a small, thin and light biomagnetism measurement device, and be arranged at high density, for example.

Although using tunnel magnetoresistive elements for a magnetic sensor can increase the density of a magnetic sensor or the like, the other above-described problems such as a problem about external magnetic fields still need to be solved.

The present invention is made in view of the above-described problems, and an object thereof is, in a case where a plurality of tunnel magnetoresistive elements are used as sensor devices to detect biomagnetic signals in order to measure magnetism emitted from a living body, to detect the biomagnetic signals with the tunnel magnetoresistive elements while cancelling out an external magnetic field or the like which is not a detection target with the tunnel magnetoresistive elements.

Means for Solving the Problems

According to a first aspect of the present invention, there is provided a magnetic sensor including a plurality of assemblies combined, each of the assemblies including a plurality of tunnel magnetoresistive elements each (i) including: a fixed magnetic layer having a fixed magnetization direction; a free magnetic layer having a changeable magnetization direction which changes by influence of a magnetic flux from outside; and an insulating layer disposed between the fixed magnetic layer and the free magnetic layer and (ii) changing a current flowing from the fixed magnetic layer to the free magnetic layer depending on an angular difference between the magnetization direction of the fixed magnetic layer and the magnetization direction of the free magnetic layer, wherein the assembly includes: the tunnel magnetoresistive elements (i) disposed in such a way that the magnetization directions of the fixed magnetic layers are substantially identical and the magnetization directions of the free magnetic layers with no magnetic field applied are substantially identical and (ii) connected to each other in series-parallel; a capacitor connected in parallel to the tunnel magnetoresistive elements which are connected to each other in series-parallel; and a fixed resistor connected in series to the tunnel magnetoresistive elements which are connected to each other in series-parallel and to the capacitor, and the assemblies are (i) disposed in such a way that the magnetization directions of the fixed magnetic layers of the assemblies have a relative angle of more than 90 degrees and (ii) connected to each other in series and/or in parallel.

Preferably, in the magnetic sensor, the relative angle is substantially 180 degrees.

Preferably, in the magnetic sensor, the assemblies are disposed at intervals of a predetermined space.

Preferably, in the magnetic sensor, in the tunnel magnetoresistive element, the magnetization direction of the free magnetic layer with no magnetic field applied and the magnetization direction of the fixed magnetic layer are different from each other.

Preferably, in the magnetic sensor, a resistance value of the fixed resistor of the assembly is 0.4R or more and 2.5R or less, wherein R[Ω] represents a resistance value of the tunnel magnetoresistive elements with no magnetic field applied, the tunnel magnetoresistive elements being connected in series to the fixed resistor in the assembly.

Preferably, in the magnetic sensor, the tunnel magnetoresistive elements and the capacitor are mounted on a same substrate, and $4.0\times10^{-5} < C \cdot R \ [\Omega \cdot F] < 4.0 \times 10^{-4}$ is satisfied, wherein R[Ω] represents a resistance value of the tunnel magnetoresistive elements with no magnetic field applied, and C[F] represents capacitance of the capacitor.

Preferably, in the magnetic sensor, the tunnel magnetoresistive elements and the fixed resistor are connected to a constant voltage source in series, and an output line for a detection signal is taken out from between the tunnel magnetoresistive elements and the fixed resistor.

Preferably, in the magnetic sensor, the substrate is any of a glass epoxy substrate, a polyimide substrate, a ceramic substrate and a glass substrate.

Preferably, in the magnetic sensor, a wire on the substrate does not include a magnetic substance.

According to a second aspect of the present invention, there is provided a biomagnetism measurement system including: a plurality of magnetic sensors described above; and an arithmetic device which generates biomagnetism information on the basis of a detection signal of the magnetic sensors.

Advantageous Effects of the Invention

According to the present invention, the assemblies having the tunnel magnetoresistive elements, the fixed magnetic layers of which are disposed to have a relative angle of at least more than 90° (preferably substantially 180°) to be opposite to each other, oppositely change their respective resistance values with respect to a large eternal magnetic field or a uniform magnetic field derived from magnetism relatively widely emitted from a human body which is not a detection target, thereby cancelling out the changes of the resistance values. Hence, a resistance value of a component in which these are connected to each other in series and/or in parallel is a constant value. On the other hand, with respect to a weak magnetic field emitted from a detection target (for example, a brain) and locally different, the assemblies show different changes of the resistance values, which are not cancelled out, and this is detected. That is, biomagnetic signals of a detection target can be detected.

EMBODIMENT FOR CARRYING OUT THE INVENTION

In the following, an embodiment of the present invention is described with reference to the drawings. The following is an embodiment of the present invention and hence does not intend to limit the present invention.

Figure 1:
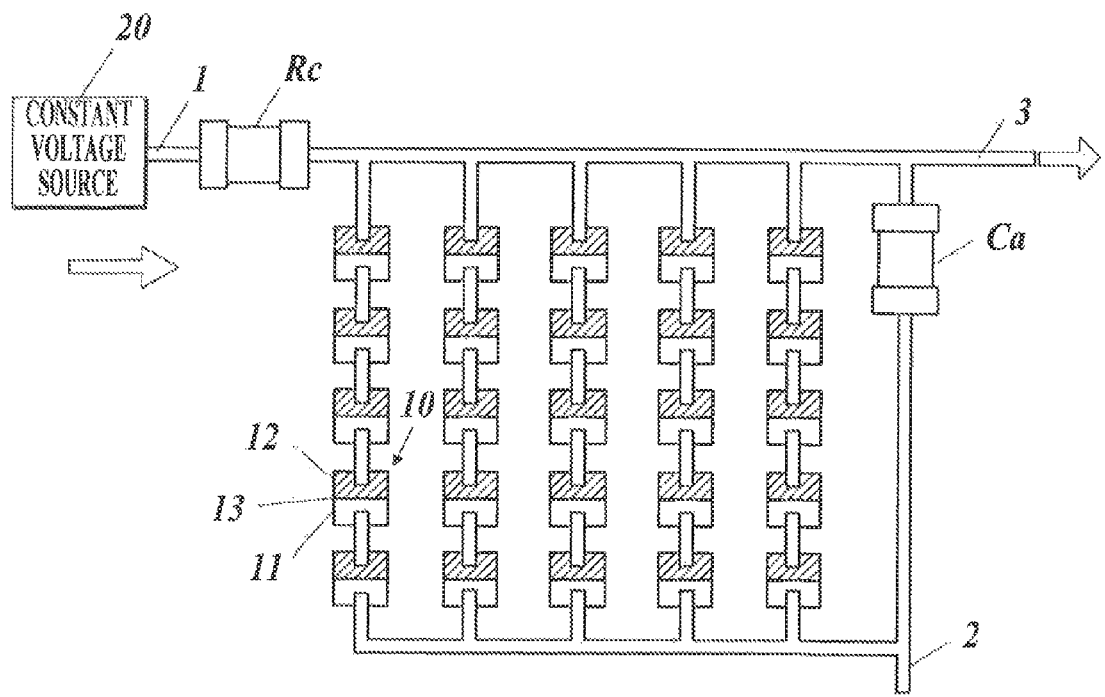
FIG. 1 is a schematic view showing a circuit configuration of an assembly according to an embodiment of the present invention.

A magnetic sensor of the embodiment is formed by combining a plurality of assemblies each having a circuit configuration shown in FIG. 1.

Each assembly includes: a plurality of tunnel magnetoresistive elements 10 connected to each other in series-parallel; a capacitor Ca connected to the tunnel magnetoresistive elements 10 in parallel; and a fixed resistor Rc connected to the tunnel magnetoresistive elements 10 and the capacitor Ca in series. Hereinafter, "in series-parallel" means that sets of tunnel magnetoresistive elements 10 connected to each other in series are connected to each other in parallel, sets of tunnel magnetoresistive elements 20 connected to each other in parallel are connected to each other in series, or a combination thereof. (Refer to FIGS. 15A to 15C.)

Each tunnel magnetoresistive element 10 has a fixed magnetic layer 11 having a fixed magnetization direction, a free magnetic layer 12 having a changeable magnetization direction which changes by influence of a magnetic flux from outside, and an insulating layer 13 arranged between the fixed magnetic layer 11 and the free magnetic layer 12.

Each tunnel magnetoresistive element 10 changes a current flowing from the fixed magnetic layer 11 to the free magnetic layer 12 depending on the angular difference between the magnetization direction of the fixed magnetic layer 11 and the magnetization direction of the free magnetic layer 12. Hence, the resistance value of the tunnel magnetoresistive element 10 changes.

In the same assembly, the magnetization directions of the fixed magnetic layers 11 of the tunnel magnetoresistive elements 10 are substantially the same. Although the ideal thereof is that the magnetization directions of the fixed magnetic layers of all the elements are the same, as long as the magnetization directions thereof are about the same without hindering biomagnetism measurement, it is acceptable.

In addition, in the same assembly, the magnetization directions of the free magnetic layers 12 of the tunnel magnetoresistive elements 10 with no magnetic field applied are substantially the same. Although the ideal thereof is that the magnetization directions of the free magnetic layers of all the elements with no magnetic field applied are the same, as long as the magnetization directions thereof with no magnetic field applied are about the same without hindering biomagnetism measurement, it is acceptable.

In the circuit configuration shown in FIG. 1, an electrode 1 is connected to the high potential side of a constant voltage source 20, an electrode 2 is connected to the ground, and the potential of an electrode 3 is output as a detection signal. When the resistance value of the tunnel magnetoresistive elements 10 changes by influence of a magnetic field, the potential of the electrode 3 changes. Hence, a magnetic field can be detected by detecting the potential thereof.

Because a large number of tunnel magnetoresistive elements are connected to each other in such a way that the magnetization directions thereof are the same as described above, individual difference among the elements is eliminated and shot noise is reduced, and also because there are a large number of tunnel magnetoresistive elements, the resistance value is dispersed, so that heat generation is reduced and thermal noise is reduced. This relates to reduction of noise internally derived, and environmental noise is reduced as described below.

The magnetic sensor is formed by combining a plurality of assemblies which are described above. The sectional view of FIG. 2A and the perspective view of FIG. 2b show an example of an assembly unit equipped with an assembly. The assembly unit is for combining a plurality of assemblies easily.

Figure 2A:
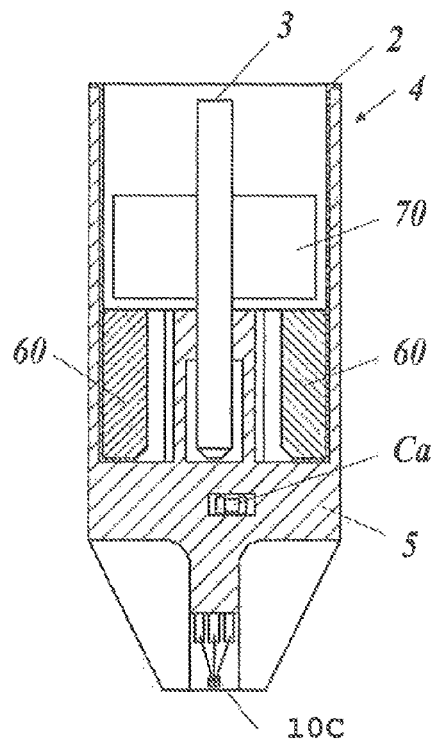
FIG. 2A is a longitudinal sectional view showing an example of an assembly unit equipped with the assembly.
Figure 2B:
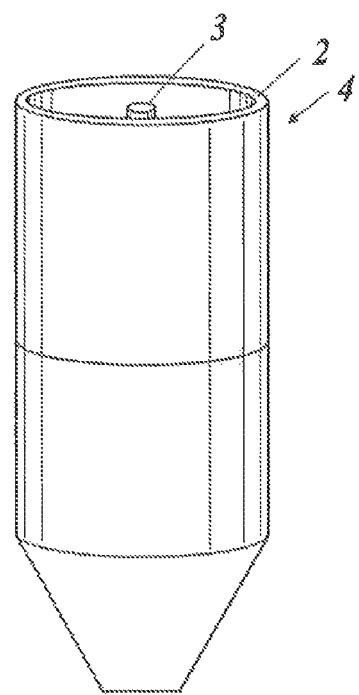
FIG. 2B is a perspective view showing the example of the assembly unit equipped with the assembly.

In an assembly unit 4 shown in FIGS. 2A and 2B, the tunnel magnetoresistive elements 10 are configured as an integrated circuit on a chip 10C, and the chip 10C and the capacitor Ca are mounted on the same substrate 5.

One end of the capacitor Ca is electrically connected to a terminal 60, and the other end of the capacitor Ca is electrically connected to the electrode 3 as an output signal terminal. The terminal 60 is electrically connected to the electrode 2 as a ground connection terminal through a metal layer formed on the inner surface of the assembly unit 4. The upper part of the assembly unit 4 is formed to be cylindrical, the metal layer connected to the terminal 60 is formed on the inner circumferential surface of the upper part thereof, and the electrode 2 is formed on the upper edge of the assembly unit 4. The electrode 3 is arranged at the center of the cylindrical upper part of the assembly unit 4. A circular insulator 70 having an opening is placed between the metal layer and the electrode 3 in such a way that the electrode 3 passes through the opening.

Figure 3A:
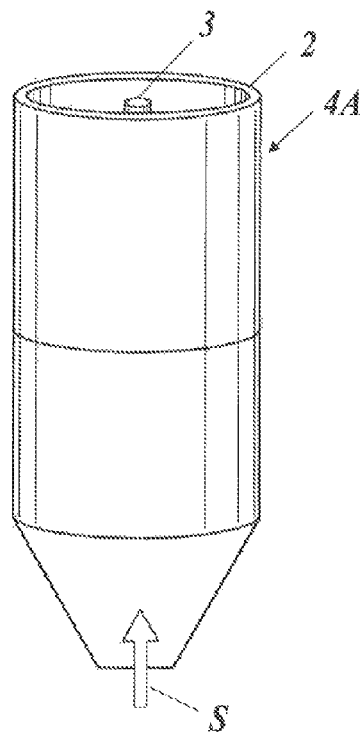
FIG. 3A is a perspective view showing one of two types of assembly units having fixed magnetic layers the magnetization directions of which are opposite to each other.

The magnetization directions of the fixed magnetic layers 11 of the tunnel magnetoresistive elements 10 formed on the chip 10C are indicated by arrows S in FIGS. 3A and 38.

Figure 3B:
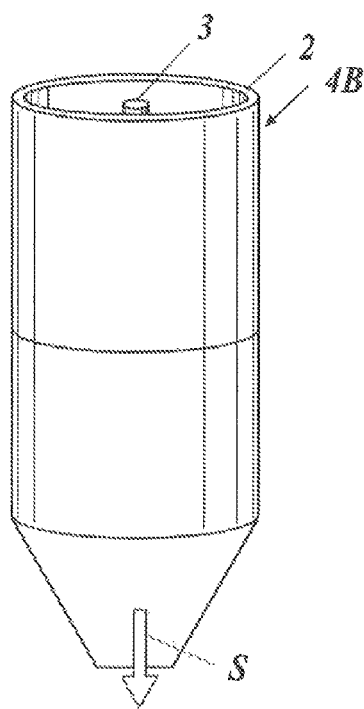
FIG. 3B is a perspective view showing the other one of two types of assembly units having fixed magnetic layers the magnetization directions of which are opposite to each other.

Two types of assembly units 4A (FIG. 3A) and 4B (FIG. 3B) are formed by mounting the chips 10C therein in directions opposite to each other so that the magnetization directions S of the fixed magnetic layers 11 of the assembly units 4A and 4B are opposite to each other.

Figure 4:
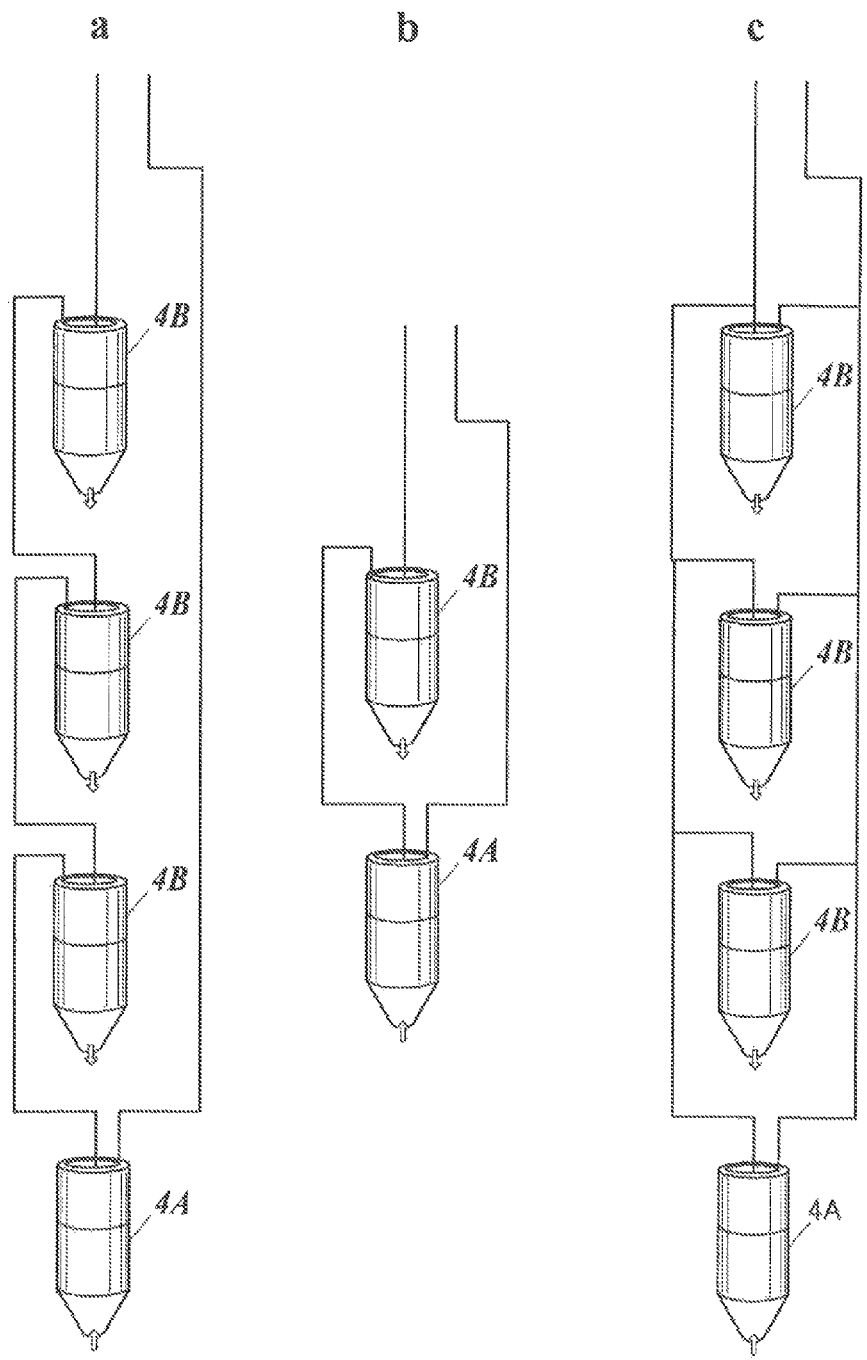
FIG. 4 is a schematic view showing examples of how to connect the assembly units to each other.

The assembly units are connected to each other. That is, the assembly unit(s) 4A and the assembly unit(s) 4B are connected to each other in series as shown in a or b of FIG. 4 to be combined. Alternatively, the assembly unit(s) 4A and the assembly unit (s) 4B are connected to each other in parallel as shown in c of FIG. 4 to be combined.

Figure 5:
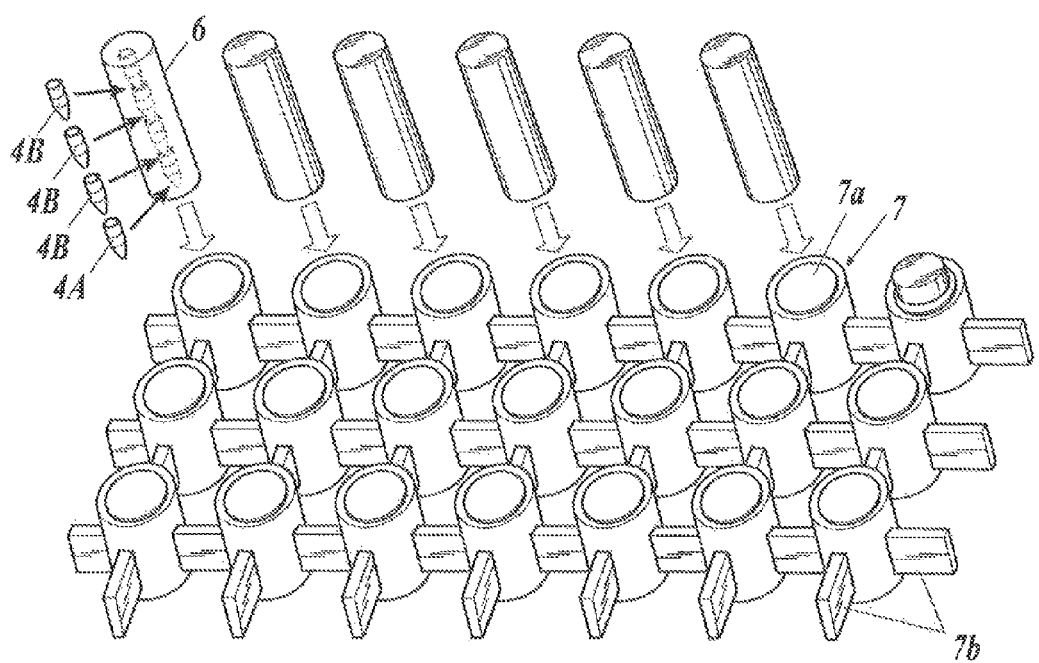
FIG. 5 is a perspective view showing an example of a component to arrange a large number of the assembly units three-dimensionally.

The relative positions of the combined assembly unit(s) 4A and assembly unit (s) 4B are kept by a fitting unit 6 shown in FIG. 5, and the assembly unit (s) 4A and the assembly unit (s) 4B are fixed in the fitting unit 6 at intervals of a predetermined space.

Figure 6:
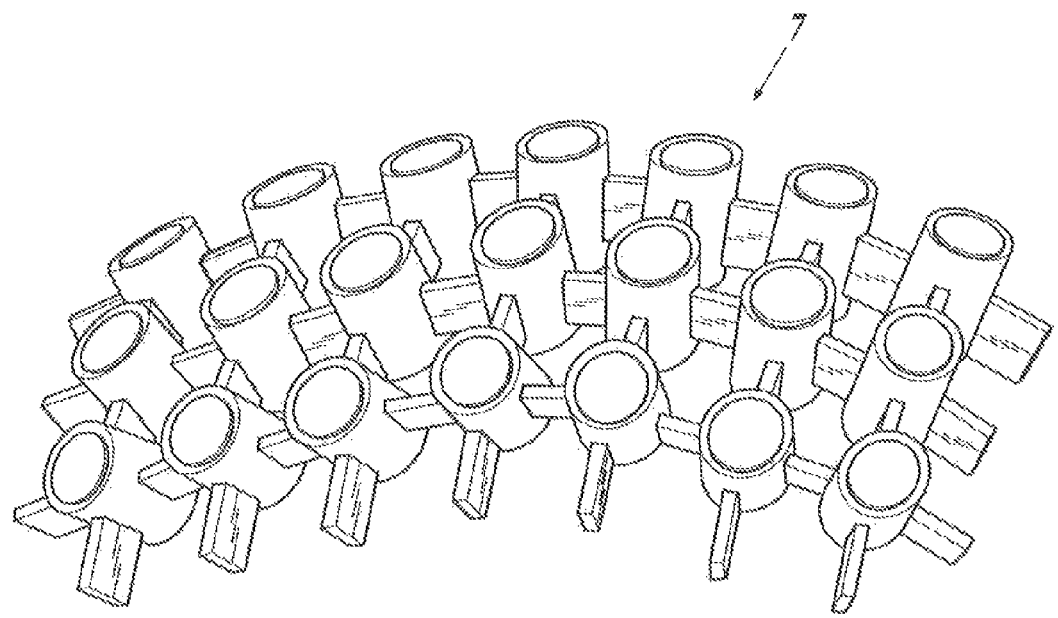
FIG. 6 is a perspective view showing that the component shown in FIG. 5 is curved.

The fitting units 6 each equipped with the assembly unit(s) 4A and the assembly unit(s) 4B are inserted into insertion parts 7a of a holding grid 7 to be arranged in a matrix and held. Stretchable joints 7b connect the insertion parts 7a and consequently, as shown in FIG. 6, a layout surface on which the fitting units 6 are arranged is curved along the surface (for example, the head) of a human body as a detection target.

Figure 7:
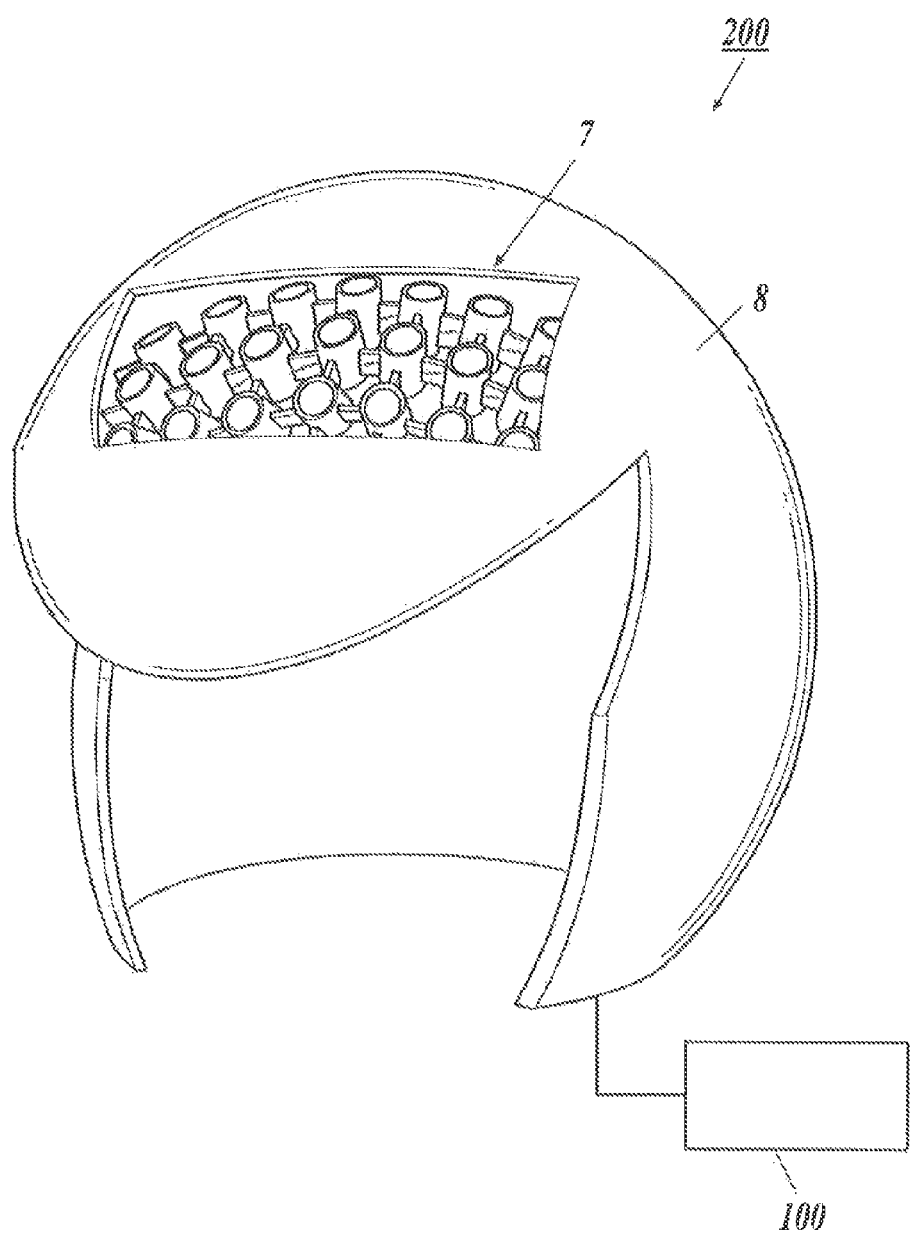
FIG. 7 is a perspective view showing an example of a component which is a helmet-type magnetic shielded device having the component shown in FIG. 5 therein.
Figure 8:
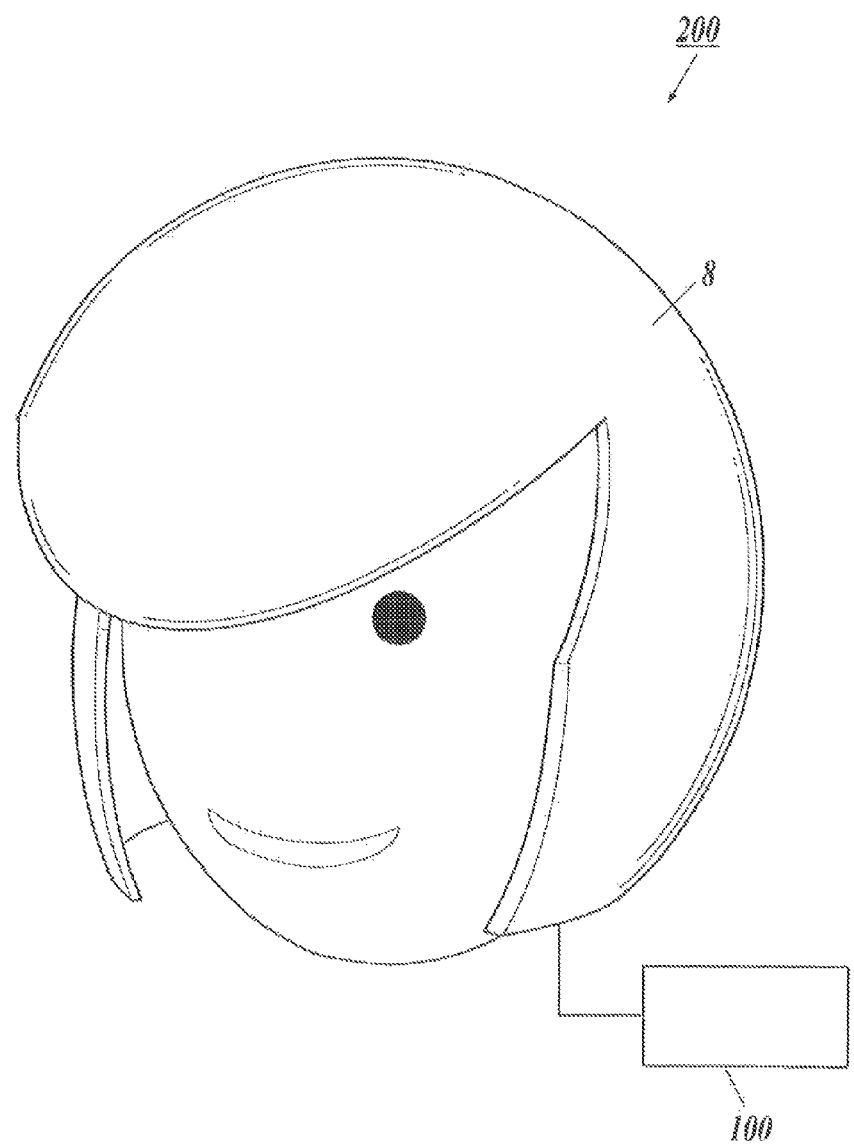
FIG. 8 is a perspective view showing that the component shown in FIG. 7 is put on the head of a subject.

In a case where a neuromagnetic field is a detection target, as shown in FIG. 7, the holding grid 7 in which the assembly units are mounted is placed in a helmet-type magnetic shielded device 8 to be put on the head of a subject, and as shown in FIG. 8, the magnetic shielded device 8 is put on the head thereof to detect biomagnetism. As a matter of course, the inner surface of the device 8 is configured in such a way that the head touches the holding grid 7 directly or through a soft material such as cloth. This is for the holding grid 7 to be curved along the skull by pressure added to the holding grid 7 from the head.

Figure 9:
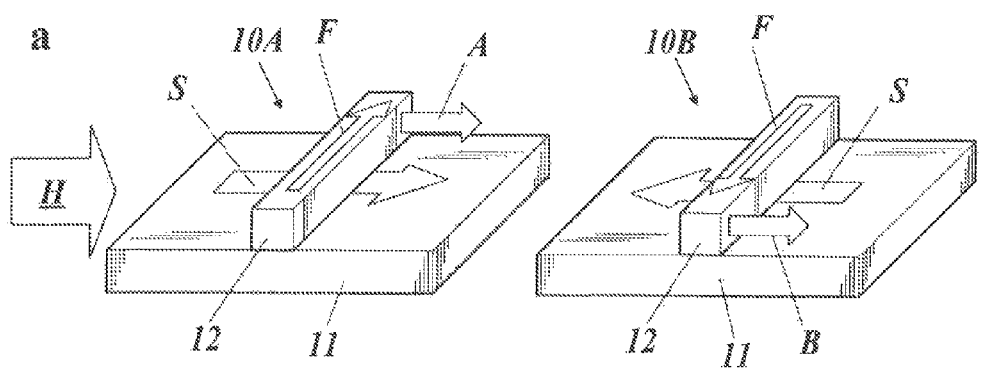
FIG. 9 shows a perspective view in a showing two tunnel magnetoresistive elements having fixed magnetic layers the magnetization directions of which are different from each other; and shows graphs in b and c showing changes of resistance values of the tunnel magnetoresistive elements.
Figure 9:
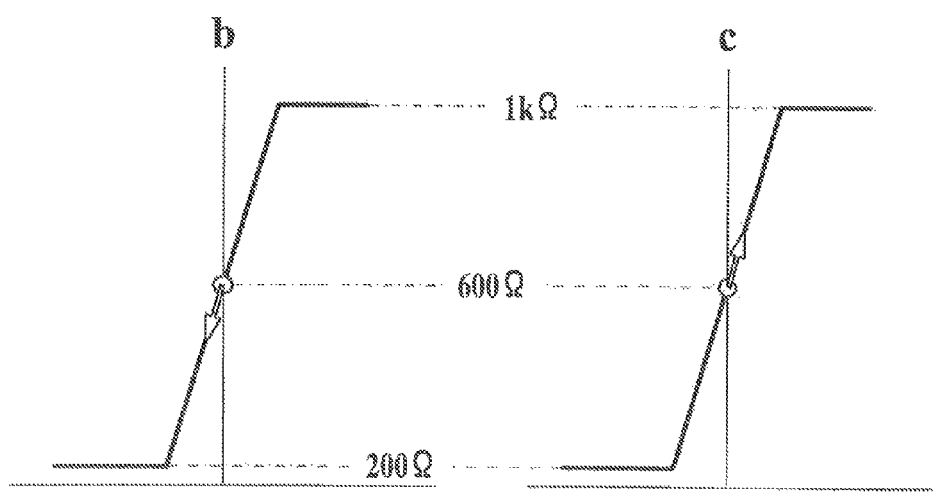

As representatives of the tunnel magnetoresistive elements 10 formed on the chips 10c in the assembly units 4A and 4B configured as described above, one tunnel magnetoresistive element 10 of each of the assembly units 4A and 4B is picked up and schematically shown in a of FIG. 9, in which an example of arrangement of the tunnel magnetoresistive elements 10 is shown.

That is, as shown in a of FIG. 9, the magnetization direction S of the fixed magnetic layer 11 of a tunnel magnetoresistive element 10A has a relative angle of 180° C. with respect to the magnetization direction S of the fixed magnetic layer 11 of a tunnel magnetoresistive element 10B, thereby being opposite to the magnetization direction S of the fixed magnetic layer 11 of the tunnel magnetoresistive element 10B.

In a of FIG. 9, the magnetization directions of the free magnetic layers 12 with no magnetic field applied are indicated by arrows F. The magnetization directions F of the free magnetic layers 12 with no magnetic field applied are different from the magnetization directions 3 of the fixed magnetic layers 11. In a of FIG. 9, they are 90° different.

In a of FIG. 9, the magnetization direction F of the free magnetic layer 12 of the tunnel magnetoresistive element 10A is opposite to the magnetization direction F of the free magnetic layer 12 of the tunnel magnetoresistive element 10B, but they may be the same. In addition, in a of FIG. 9, the free magnetic layers 12 are on the upper side, and the fixed magnetic layers 11 are on the lower side. However, this is not a limitation, and hence positions of the free magnetic layers 12 and the fixed magnetic layers 11 may be reversed from those shown in a of FIG. 9.

When a large magnetic field H is applied to these tunnel magnetoresistive elements 10A and 10B due to an external magnetic field or the like, the magnetization direction F of the free magnetic layer 12 of the tunnel magnetoresistive element 10A swings to a direction indicated by an arrow A, and the magnetization direction F of the free magnetic layer 12 of the tunnel magnetoresistive element 10B swings to a direction indicated by an arrow B.

At the time, in the tunnel magnetoresistive element 10A, the direction A to which the magnetization direction F of the free magnetic layer 12 swings is the same as the magnetization direction S of the fixed magnetic layer 11, and in the tunnel magnetoresistive element 10B, the direction B to which the magnetization direction F of the free magnetic layer 12 swings is opposite to the magnetization direction S of the fixed magnetic layer 11.

In a tunnel magnetoresistive element 10, when the magnetization direction F of the free magnetic layer 12 swings to a direction which is the same as the magnetization direction S of the fixed magnetic layer 11, the resistance value decreases, and when the magnetization direction F thereof swings to a direction which is opposite to the magnetization direction S thereof, the resistance value increases.

Hence, as shown in b of FIG. 9, the resistance value of the tunnel magnetoresistive element 10A decreases, and as shown in c of FIG. 9, the resistance value of the tunnel magnetoresistive element 10B increases. The resistance value of a tunnel magnetoresistive element 10 changes within a predetermined range (for example, 200Ω to 1 kΩ) depending on the strength of the magnetic field H. When the same magnetic field H is applied to the tunnel magnetoresistive element 10A and the tunnel magnetoresistive element 10B, fluctuations of their resistance values are the same, and hence the combined resistance value thereof does not change and shows a constant value. Thus, a fitting unit 6 is formed in such a way that the combined resistance of the fitting unit 6 does not change when the same magnetic field acts on the tunnel magnetoresistive elements 10 in the fitting unit 6.

With the above-described principle, a fitting unit 6 functions as a magnetic sensor having a function to cancel out noise such as an external magnetic field.

With the configuration described above, the resistance values cancel each other out, and accordingly noise cancellation is performed. More specifically, even when a large magnetic field existing in the nature world or a magnetic field widely emitted from a human body is detected, as described above, the resistance values of the elements 10A and 10B have different signs and the absolute values of the resistance values thereof are the same, so that it is possible to make the resistance values cancel each other out and not to output the resistance values as the magnetism detection signal.

On the other hand, a weak magnetic field emitted from a detection target (for example, a brain) acts on the assembly units 4A and 4B, which are different, in a fitting unit 6 differently because magnetic flux densities/magnetic field strengths thereto are different. That is, the change of the resistance value of one of them is large, and the change of the resistance value of the other of them is small, so that imbalance occurs. Similarly, when a large number of assembly units are connected to each other, the changes of the resistance values of some assembly units are large, and the changes of the resistance values of the other assembly units are small.

Hence, with respect to a weak magnetic flux close to a sensor constituted of assemblies combined, the absolute values of the resistance values output from both types of the assemblies are different, and the magnetism detection signal, which is the total of the resistance values, changes from zero. As described above, because the large magnetic field, which is noise, is cancelled out, only the small magnetic field, which is a detection target, can be extracted as the magnetism detection signal.

This principle of noise cancellation is described again with reference to FIGS. 10 and 11. A case is described where the base elements of a magnetic sensor are a tunnel magnetoresistive element 10m and a tunnel magnetoresistive element 10n arranged therein as shown in a1 of FIG. 10. The tunnel magnetoresistive element 10m and the tunnel magnetoresistive element 10n are arranged close to each other, having a predetermined space therebetween in a pile direction in which their respective fixed magnetic layers 11 and their respective free magnetic layers 12 are piled. In a of FIG. 9, they are arranged close to each other in such a way that their respective fixed magnetic layers 11 and their respective free magnetic layers 12 are each arranged on the same level, having a predetermined space therebetween. However, when they are arranged as described above having a predetermined space therebetween in the pile direction too, the advantageous effects described above can be obtained.

Figure 10:
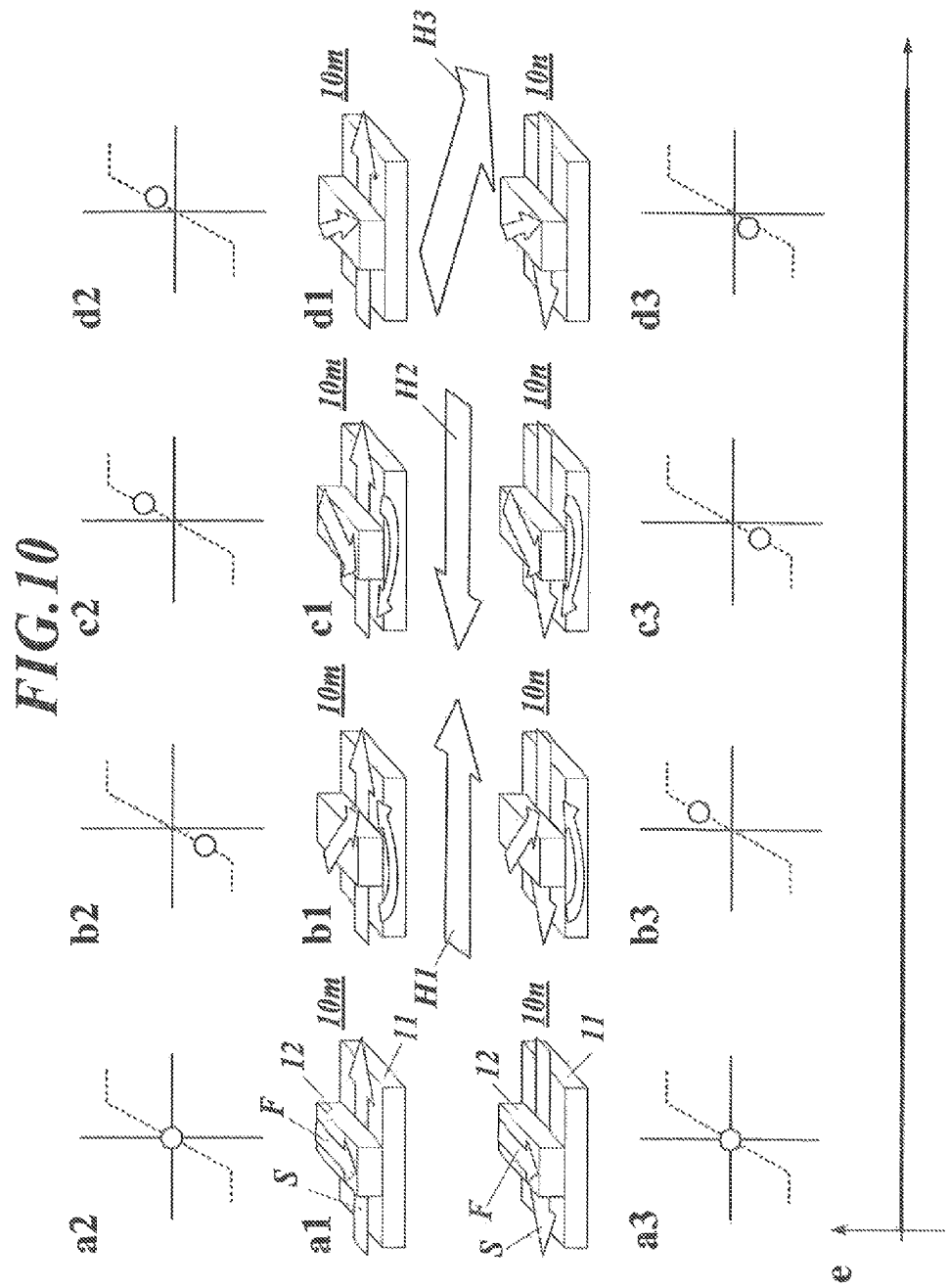
FIG. 10 shows perspective views in a1, b1, c1 and d1 each showing two tunnel magnetoresistive elements having fixed magnetic layers the magnetization directions of which are different from each other; shows graphs in a2, b2, c2 and d2 and a3, b3, c3 and d3 showing changes of resistance values of the tunnel magnetoresistive elements; and shows a graph in e showing combined resistance.

The magnetization direction S of the fixed magnetic layer 11 of the tunnel magnetoresistive element 10m has a relative angle of 180° with respect to the magnetization direction S of the fixed magnetic layer 11 of the tunnel magnetoresistive element 10n, thereby being opposite to the magnetization direction S of the fixed magnetic layer 11 of the tunnel magnetoresistive element 10n. The a1 of FIG. 10 shows a state in which no magnetic field is applied. In this state, the magnetization directions F of the free magnetic layers 12 intersect with the magnetization directions S of the fixed magnetic layers 11 at 90°, and the magnetization direction F of the free magnetic layer 12 of the tunnel magnetoresistive element 10m and the magnetization direction F of the free magnetic layer 12 of the tunnel magnetoresistive element 10n are the same but may be opposite to each other.

In a case where the relative angle of the magnetization directions of the two tunnel magnetoresistive elements 10m and 10n is 180°, the relative angle may be exactly 180° or a little different from 180° within a range of angles which can be substantially regarded as 180°. More specifically, when the relative angle is within a range of 180°±3° or so, the relative angle can be substantially regarded as 180°.

The b1, c1 and d1 of FIG. 10 show configurations each of which is the same as that shown in a1 of FIG. 10, with different magnetic fields. The a2, b2, c2 and d2 of FIG. 10 show the change of the resistance value of the tunnel magnetoresistive element 10m in the states shown in a1, b1, c1 and d1 of FIG. 10. The a3, b3, c3 and d3 of FIG. 10 show the change of the resistance value of the tunnel magnetoresistive element 100n in the states shown in a1, b1, c1 and d1 of FIG. 10. The e of FIG. 10 shows the combined resistance of a circuit in the states shown in a1, b1, c1 and d1 of FIG. 10, the circuit in which the tunnel magnetoresistive elements 10m and 10n are connected to each other in series or in parallel.

As shown in b1, c1 and d1 of FIG. 10, when a large magnetic field H1, H2 or H3 having different directions is generated, the magnetization directions F of the free magnetic layers 12 of the elements 10m and 10n each swing differently depending on the magnetic field. However, the resistance values of the elements 10m and 10n make opposite changes and hence the combined resistance is constant. This is the principle of cancellation of a large magnetic field as noise.

Figure 11:
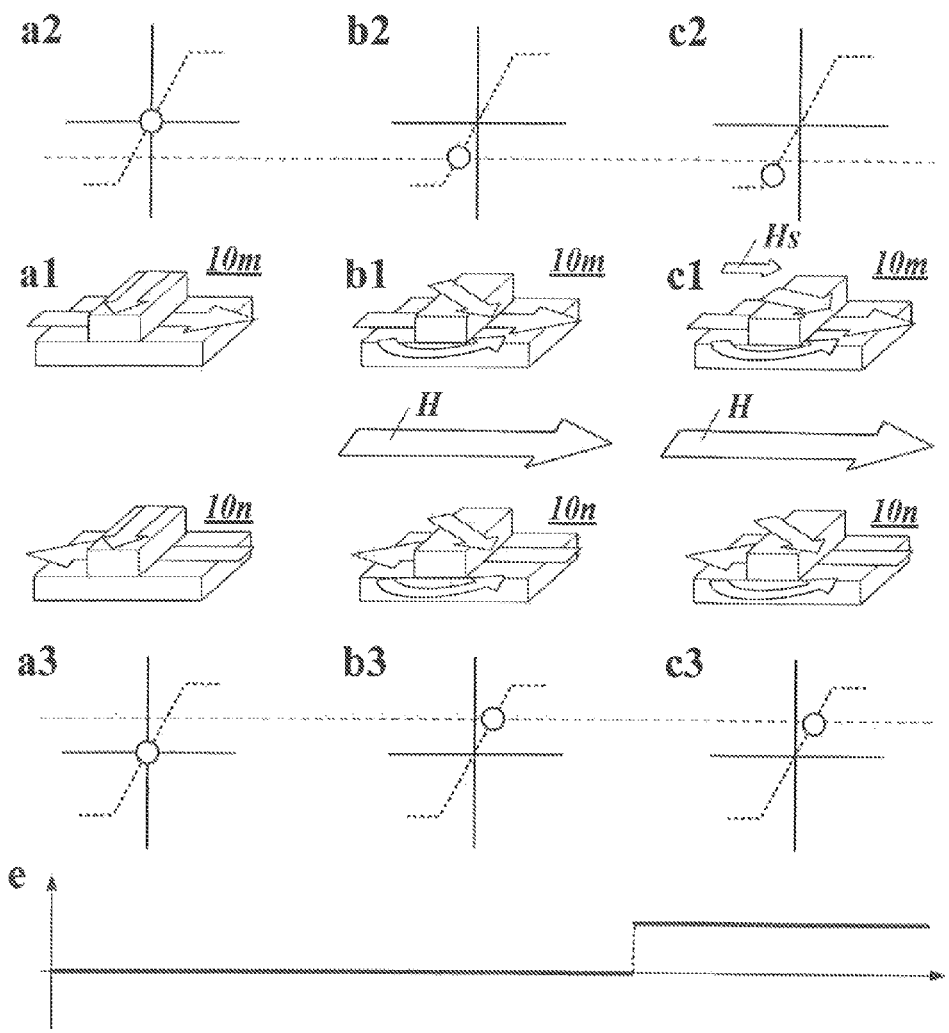
FIG. 11 shows perspective views in a1, b1 and c1 each showing the two tunnel magnetoresistive elements having fixed magnetic layers the magnetization directions of which are different from each other; shows graphs in a2, b2 and c2 and a3, b3 and c3 showing changes of resistance values of the tunnel magnetoresistive elements; and shows a graph in e showing combined resistance.

FIG. 11 shows an illustration similar to that of FIG. 10. However, in c1 of FIG. 11, a small magnetic field Hs which influences the tunnel magnetoresistive element 10m more is generated. The small magnetic field Hs corresponds to a magnetic field emitted from a detection target such as a brain.

While no magnetic field is generated in a1 of FIG. 11, the large magnetic field H, which influences the elements 10m and 10b equally, is generated in b1 of FIG. 11. In this case, the combined resistance does not change and is constant. As confirmed with reference to FIG. 10, regardless of the direction of the magnetic field H, this is true. Under such a situation, when the small magnetic field Hs is generated at the position of the element 10m as shown in c1 of FIG. 11, the resistance value of the element 10m changes as shown in c2 of FIG. 11, but the resistance value of the element 10n hardly changes as shown in c3 of FIG. 11 because the element 100n is away from the small magnetic field Hs and hardly influenced thereby. Thus, the magnetic field Hs, namely, biomagnetic signals of a detection target, can be detected while the magnetic field H, namely, a large magnetic field existing in the natural world or a magnetic field widely emitted from a human body's part (for example, a heart) which is not a detection target, is cancelled out. In the above embodiment, a plurality of assemblies are arranged in such a way that the magnetization directions of the fixed magnetic layers of the assemblies have a relative angle which is substantially 180° C. However, this is not a limitation. As long as the assemblies are arranged in such a way that the magnetization directions of the fixed magnetic layers of the assemblies have a relative angle of more than 90° C., it is acceptable.

In the configuration shown in FIGS. 5 to 7, the assembly units 4 held in a fitting unit 6 are arranged in a direction away from the surface of a living body with a part as a detection target.

With this arrangement, magnetic fields in the depth direction from the surface of a living body with the part can be detected.

When the second assembly unit 4, the third assembly unit 4 and so forth are arranged in a direction away from the first assembly unit 4 closest to a detection target, these assembly units 4 are arranged in such a way that spaces between the assembly units 4 correspond to depths where the detection target exists from the surface. That is, when a magnetic flux existing 30 mm deep from the surface of a living body is desired to be detected, the first assembly unit 4 and the second assembly unit 4 are arranged in such a way that the distance between the first assembly unit 4 and the second assembly unit 4 is 30 mm. By arranging the third assembly unit 4 and the fourth assembly unit 4 further away from the first assembly unit 4, magnetic fluxes existing in depths corresponding to distances between the assembly units 4 can be detected.

A large number of fitting units 6 each of which hold assembly units 4 in relation to the depth direction as described above are arranged in a grid along the surface of a living body as shown in FIGS. 5 to 7. Thereby, a magnetic field of a detection target can be caught three-dimensionally. The output electrodes 3 of the assembly units 4 are connected to an arithmetic device 100, and output signals from the assembly units 4 are input into the arithmetic device 100. The arithmetic device 100 converts the input signals into digital data and generates by mathematical operations data which shows three-dimensional positions (positions in a direction along the skull and in a depth direction of the head) of sources of biomagnetic signals, strength of biomagnetism and the like. For example, the arithmetic device 100 generates biomagnetism data which shows three-dimensional magnetic field distribution and outputs this data to an output device such as a display to display the data in graphics thereon. With the above-described configuration, a biomagnetism measurement system 200 is realized.

The component shown in FIG. 7 is an example used for detection of neuromagnetic fields. However, a living body's part as a detection target is not limited thereto. Although the configuration shown in FIGS. 5 to 7 is a noninvasive configuration by which the assembly units 4 facing and being the closest to a living body are in contact with the surface of the living body, the tips where the assembly units 4 are placed each may be formed in the shape of a needle having a very small diameter and invasively inserted into a living body or puncture a living body.

The capacitor Ca connected to the tunnel magnetoresistive elements 10 in parallel in the assembly shown in FIG. 1 is for cutting off high frequency environment noise from the output electrode 3. For this, the following configuration condition is effective.

The maximum value of biomagnetic signals exists in around 400[Hz] to 2[kHz]. Although it is preferable that the frequency band equal to or more than this upper limit be removed as noise, if the cutoff frequency is set to the upper limit of 2[kHz] or around, necessary signals may be distorted. Hence, in the embodiment, the upper limit of cutoff frequencies is set to 4[kHz] to sufficiently reduce noise and certainly avoid the signal distortion.

When the capacitor Ca is connected thereto, the cutoff frequency is expressed by the following formula 1.

$$f = 1/2(2\pi RC) \quad \text{(Formula 1)}$$

The maximum value of biomagnetic signals exists in around 400 [Hz] to 2 [kHz]. Although it is preferable that the frequency band equal to or more than this upper limit be removed as noise, if the cutoff frequency is set to the upper limit of 2 [kHz] or around, necessary signals may be distorted. Hence, in the embodiment, the upper limit of cutoff frequencies is set to 4 [kHqz] to sufficiently reduce noise and certainly avoid the signal distortion.

When this is replaced by C·R with the formula 1, the following formula 2 holds.

$$4.0 \times 10^{-5} < C \cdot R [\Omega \cdot F] < 4.0 \times 10^{-4} \quad \text{(Formula 2)}$$

Figure 12:
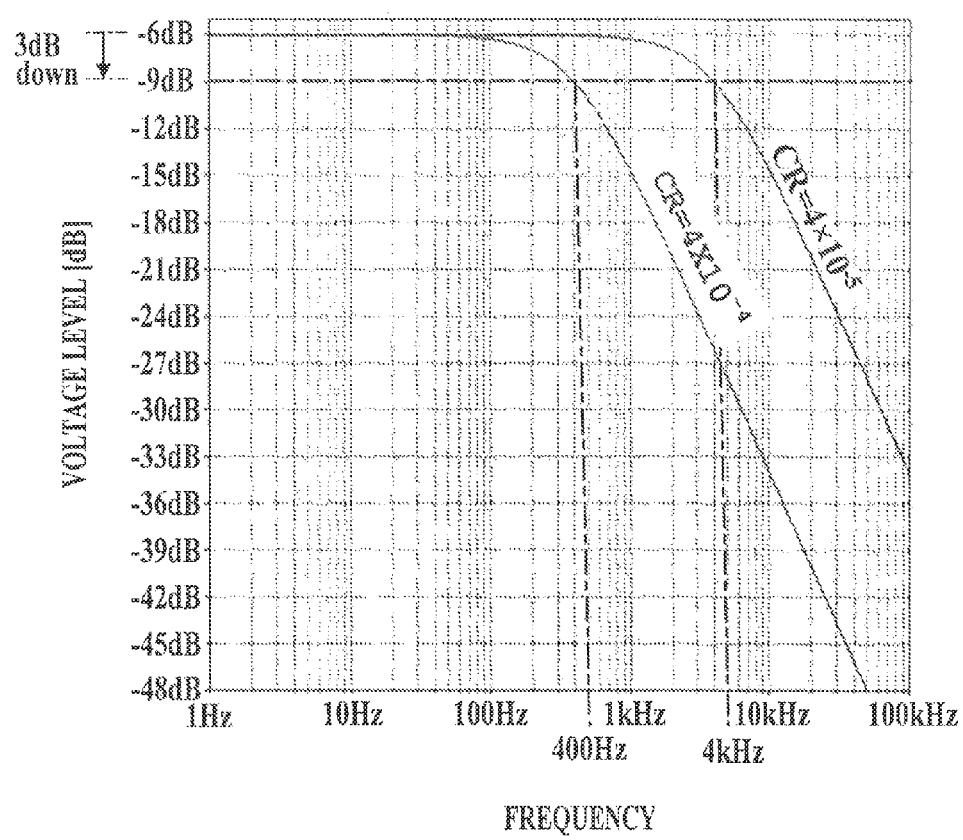
FIG. 12 is a graph showing a voltage-decay to frequency characteristic of a magnetic sensor according to the embodiment of the present invention.

When the resistance value R of the tunnel magnetoresistive elements is set to 1 [kΩ], the capacitance value C of the capacitor satisfying the formula 2 is 0.04 [μF] to 0.4 [μF]. FIG. 12 shows in a form of a graph a voltage-decay to frequency characteristic at between the ground electrode 2 and the output electrode 3 with respect to the constant voltage source 20 (connected to the electrode i) when C·R[Ω·F]=4.0×10$^{-5}$ and C·R[Ω·F]=4.0×10$^{-4}$. In the graph shown in FIG. 12, the vertical axis indicates the voltage-decay rate with respect to the constant voltage source 20.

In the graph shown in FIG. 12, a frequency 3 [dB] down from the highest value, which is flat in a relatively low frequency band, is taken as the cutoff frequency. Hence, the cutoff frequency is 4 [kHz] when C·R[Ω·F]=4.0×10$^{-5}$ and 400 [Hz] when C·R[Ω·F]=4.0×10$^{-4}$. The graph shown in FIG. 12 is created as an example by changing the capacitance value C of the capacitor Ca with the resistance value of the fixed resistor Rc being 1 [kΩ] and the resistance value R of the tunnel magnetoresistive elements 10 being 1 [kΩ].

With the above-described simple configuration including the parallel-connected capacitor, a decay of 10 [dB] to 30 [dB] at 10 [kHz] and a decay of 30 [dB] to 50 [dB] at 100 [kHz] are achieved, and the high frequency environmental noise can be reduced in the output of the tunnel magnetoresistive elements. It is preferable that at least the tunnel magnetoresistive elements 10 and the capacitor Ca be mounted on the same substrate. As the substrate, one of a glass epoxy substrate, a polyimide substrate, a ceramic substrate and a glass substrate is selected to use, and as wires on the substrate, wires made of a conductive material not including a magnetic substance are used. For example, as the wires, a Cu layer plated with Au is used, and no magnetic layer such as Ni is provided. This is to avoid influence thereof on the biomagnetism detection signal.

In order to amplify the detection signal, it is preferable that the resistance value of the fixed resistor Rc be 0.4R or more and 2.5R or less.

Figure 13:
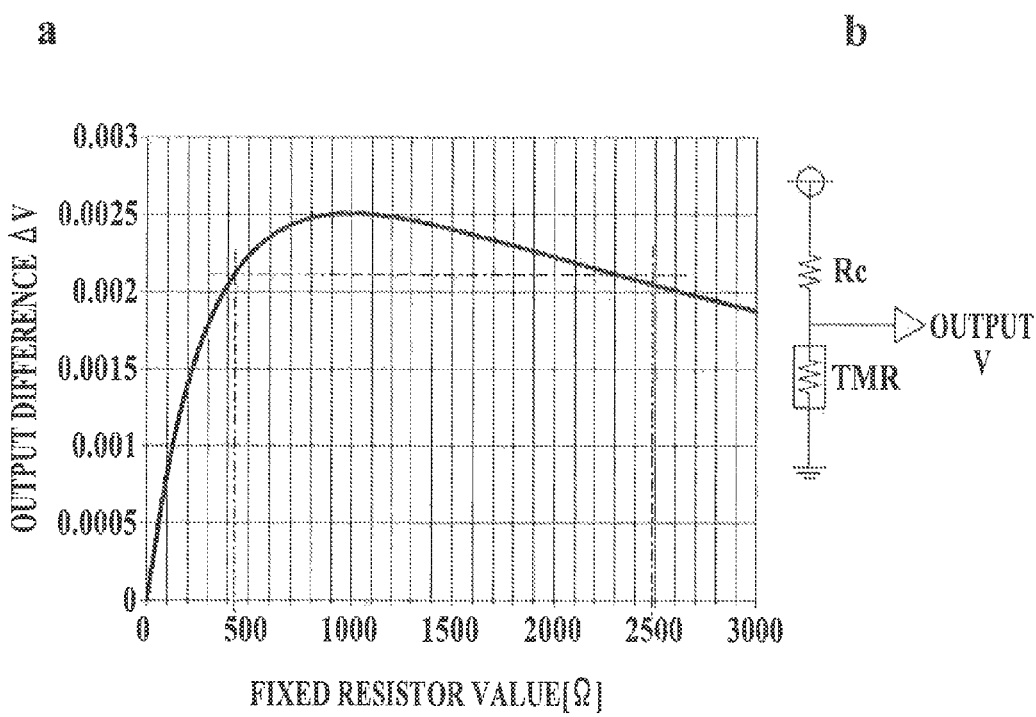
FIG. 13 shows a graph in a showing a relationship between a resistance value of a fixed resistor connected to the tunnel magnetoresistive elements in series and a change ΔV of an output V when a resistance value of the tunnel magnetoresistive elements changes by 0.01%; and shows a circuit diagram in b which is a target for measuring the relationship.

The tunnel magnetoresistive elements change the resistance value by being influenced by a magnetic field. In the circuit shown in b of FIG. 13, when the resistance value of the tunnel magnetoresistive (TMR) elements changes, the output V changes. Hence, with this output V, the change of a magnetic field where the tunnel magnetoresistive (TMR) elements are placed can be detected. The a of FIG. 13 shows the characteristic of the change ΔV of the output V with respect to the resistance value of the fixed resistor Pc when the resistance value of the tunnel magnetoresistive (TMR) elements changes by 0.01% in the circuit shown in h of FIG. 13. The initial resistance value of the tunnel magnetoresistive (TMR) elements is 1000 [Ω] and the output difference between before and after the resistance value thereof changes by 0.01% is represented by ΔV. When the resistance value of the fixed resistor Rc is 1000 [Ω], the output difference ΔV is approximately the maximum value. At the time, the resistance value of the fixed resistor Rc is 1.0 times as high as the initial resistance value of the tunnel magnetoresistive (TMR) elements. It can be seen that when the resistance value of the fixed resistor Rc is 400[Ω] to 2500[Ω], namely, within a range of values which are 0.4 times to 2.5 times as high as the initial resistance value of the tunnel magnetoresistive (TMR) elements, the output difference ΔV is more than about 80% of the maximum value, and a very small change of the resistance value of the tunnel magnetoresistive (TMR) elements is conveyed with a large output difference ΔV.

Hence, it is preferable that with respect to the resistance value R of the tunnel magnetoresistive elements 10 in an assembly with no magnetic field applied, the resistance value of the fixed resistor Rc be 0.4R or more and 2.5R or less. Accordingly, the biomagnetism detection signal can be extracted with a large change.

Because biomagnetic signals are of a low frequency band, a high-precision biomagnetism measurement system can be realized by cutting off high frequency signals with the above-described series-arranged fixed resistor Rc and parallel-arranged capacitor Ca and cancelling out the signals derived from a magnetic field which is not a detection target but having the frequency similar to that of a living body with two or more tunnel magnetoresistive elements (10A and 10B shown in FIG. 9 or 10m and 10n shown in FIG. 10 or 11) as described above.

The tunnel magnetoresistive elements are micro-sensors, and hence miniaturization of the system is possible. In addition, as described above, by using a large number of the units, the tunnel magnetoresistive elements can be arranged two-dimensionally and even three-dimensionally at high density on a living body, and hence spatial resolution is improved and the high precision is achieved from this aspect too.

[Modifications]

Figure 14:
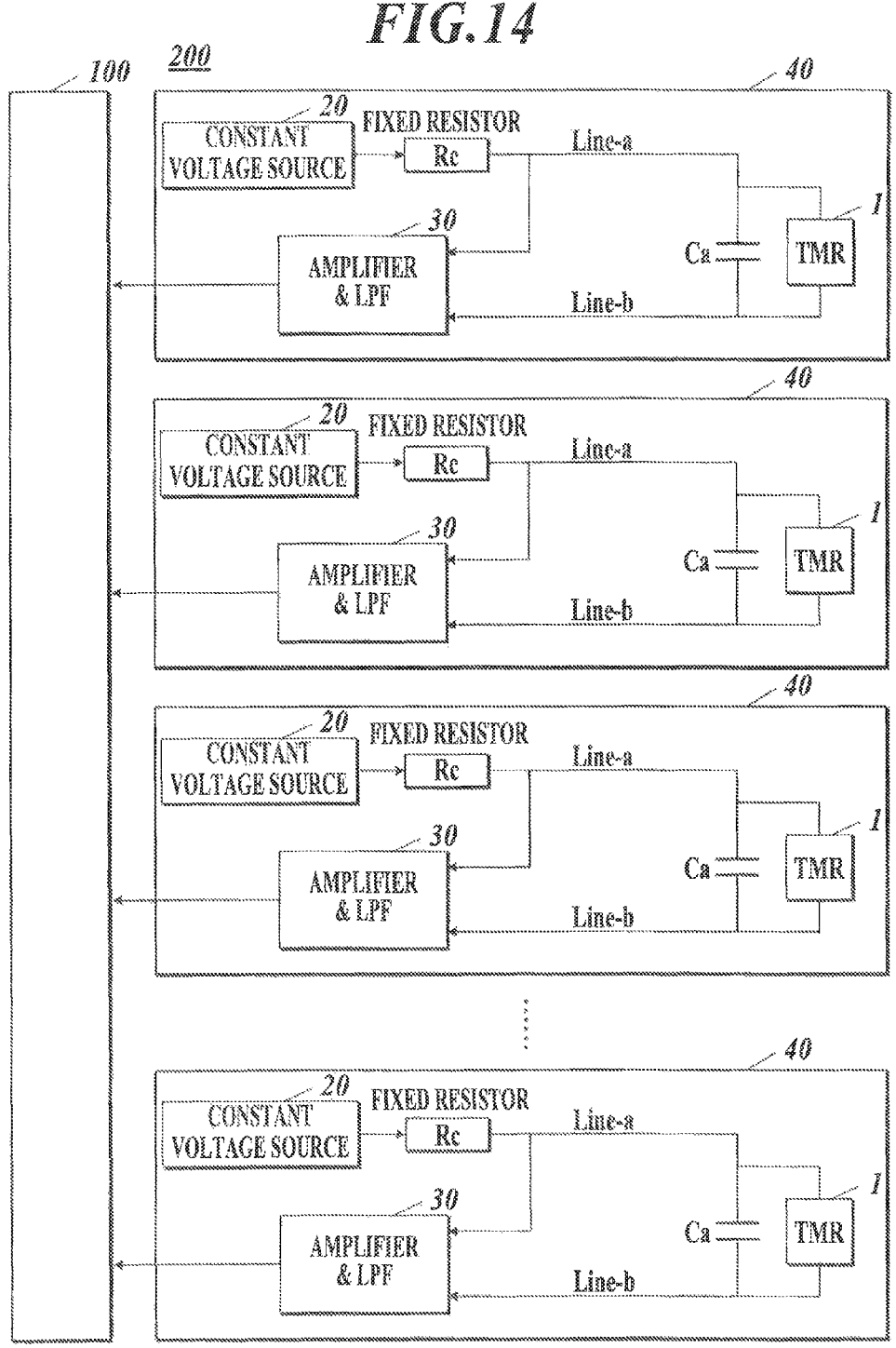
FIG. 14 is a block circuit diagram of a biomagnetism measurement system according to a modification from the embodiment of the present invention.

In the above-described biomagnetism measurement system 200, the above-described assemblies each may further have a preamplifier unit 30 constituted of an amplifier circuit and a low-pass filter (LPF) circuit. (These are shown in FIG. 14 as assemblies 40.) That is, an assembly 40 may include a TMR module 1, a fixed resistor Rc, a constant voltage source 20, a preamplifier unit 30 and a capacitor Ca as shown in FIG. 14. The TRM module 1 is constituted of tunnel magnetoresistive elements 10 connected to each other in series-parallel as described above with reference to FIG. 1.

In the assembly 40, as shown in FIG. 14, the TMR module 1 and the capacitor Ca are connected to each other in parallel. The constant voltage source 20 is connected to one end of the TMR module 1 and one end of the capacitor Ca through the fixed resistor Rc. Connection conductive lines (Line-a and Line-b) connecting the ends of the TMR module 1 with the ends of the capacitor Ca are connected to the input of the preamplifier unit 30. A plurality of such assemblies 40 are provided, and the outputs of the preamplifier units 30 of the assemblies 40 are connected to the input of an arithmetic device 100. Thus, the biomagnetism measurement system 200 is configured. The TMR modules 1 of the assemblies 40 are arranged on a living body (for example, the head or chest of a human body) to detect biomagnetic signals. The output signals from the preamplifier units 30 which are for the TMR modules 1 are input into the arithmetic device 100, and the arithmetic device 100 calculates and estimates positions of sources of biomagnetic signals, strength of biomagnetism and the like on the basis of the output signals.

As described above, at least the TMR module 1 and the capacitor Ca are mounted on the same substrate. As the substrate, one of a glass epoxy substrate, a polyimide substrate, a ceramic substrate and a glass substrate is selected to use, and as wires on the substrate, wires made of a conductive material not including a magnetic substance are used. For example, as the wires, a Cu layer plated with Au is used, and no magnetic layer such as Ni is provided. This is to avoid influence thereof on the biomagnetism detection signal.

Figure 15A:
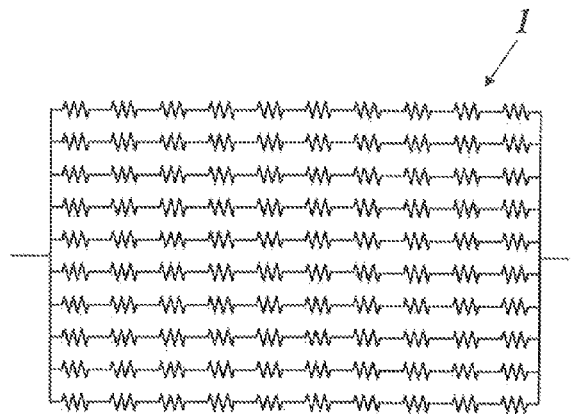
FIG. 15A shows an example of an equivalent circuit schematic of a TMR module according to the modification from the embodiment of the present invention.
Figure 15B:
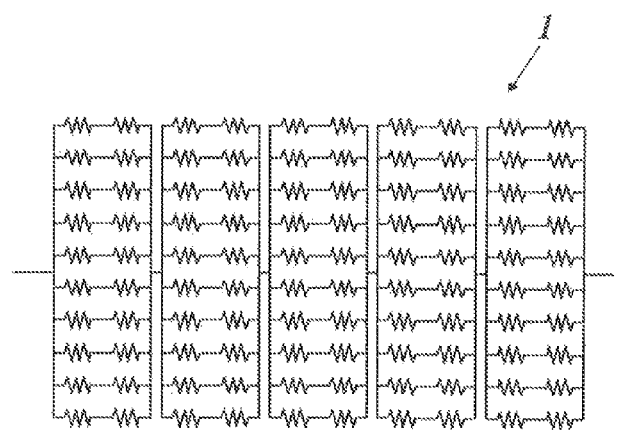
FIG. 15B shows an example of the equivalent circuit schematic of the TMR module according to the modification from the embodiment of the present invention.
Figure 15C:
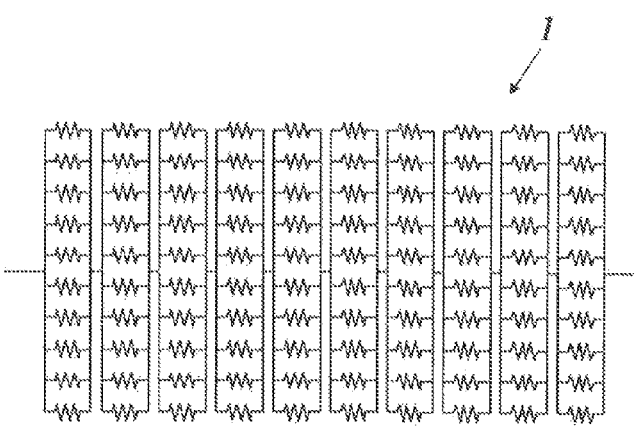
FIG. 15C shows an example of the equivalent circuit schematic of the TMR module according to the modification from the embodiment of the present invention.

When each tunnel magnetoresistive element 10 is shown as a resistor, the TMR module 1 is constituted of a plurality of tunnel magnetoresistive elements 10 connected to each other in series and/or in parallel as shown in FIGS. 15A to 15C as examples.

The TMR module 1 shown in FIG. 15A is configured in such a way that sets of tunnel magnetoresistive elements 10 connected to each other in series are connected to each other in parallel. The TMR module 1 shown in FIG. 15B is configured in such a way that sets of tunnel magnetoresistive elements 10 connected to each other in series are connected to each other in parallel and groups of such sets are connected to each other in series. The TMR module 1 shown in FIG. 15C is configured in such a way that sets of tunnel magnetoresistive elements 10 connected to each other in parallel are connected to each other in series. Regardless of how to connect tunnel magnetoresistive elements 10 to each other, connecting tunnel magnetoresistive elements 10 to each other in parallel reduces shot noise and quantization noise as the whole TMR module 1, and connecting tunnel magnetoresistive elements 10 to each other in series reduces thermal noise and quantization noise as the whole TMR module 1.

Figure 16:
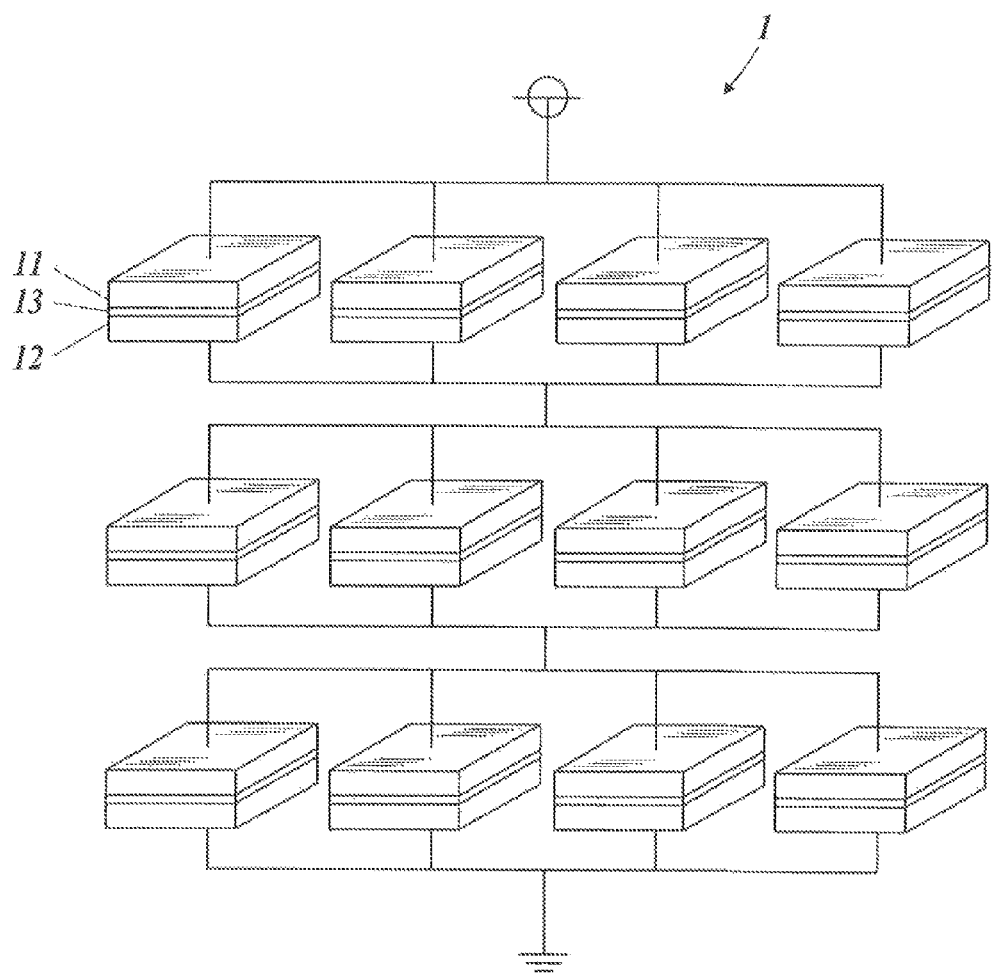
FIG. 16 shows tunnel magnetoresistive elements in a three-dimensional model in arm example of the equivalent circuit schematic of the TMR module according to the modification from the embodiment of the present invention.

The structure of each tunnel magnetoresistive element 10 of the TMR module 1 is described above. That is, each tunnel magnetoresistive element 10 has a fixed magnetic layer 11 (or 12) having a fixed magnetization direction, a free magnetic layer 12 (or 11) having a changeable magnetization direction which changes by influence of a magnetic flux from outside, and an insulating layer 13 arranged between the fixed magnetic layer and the free magnetic layer, and acts to change the resistance of the insulating layer 13 by the tunnel effect depending on the angular difference between the magnetization direction of the fixed magnetic layer and the magnetization direction of the free magnetic layer (see FIG. 16).

Further, as a measure to reduce the high frequency environmental noise, a configuration condition is made. The configuration condition is to satisfy $4.0 \times 10^{-5} < C \cdot R[\Omega \cdot F] < 4.0 \times 10^{-4}$, wherein $R[\Omega]$ represents the resistance value of the TMR module 1 with no magnetic field applied, and $C[F]$ represents the capacitance of the capacitor Ca.

The cutoff frequency at the both ends of the TMR module 1 (herein, a frequency to which the frequency of an input signal is changed and at which the output from the TMR module 1 can be regarded as being sufficiently small) shown in FIG. 14 is expressed by the above-mentioned formula 1 ($f=1/(2\pi RC)$), wherein R represents the resistance value of the TMR module 1 with no magnetic field applied. As described above, the maximum value of biomagnetic signals exists in around 400 [Hz] to 2 [kHz]. Hence, when the cutoff frequency is set to 400 [Hz] to 4 [kHz] to sufficiently reduce noise and certainly avoid the signal distortion, and this is replaced by C·R with the formula 1, the above-mentioned formula 2 ($4.0 \times 10^{-5} < C \cdot R[\Omega \cdot F] < 4.0 \times 10^{-4}$) holds. The simulation result of the voltage-decay to frequency characteristic at the both ends of the TMR module 1 with respect to the constant voltage source 20 when $C \cdot R[\Omega \cdot F] = 4.0 \times 10^{-5}$ and $C \cdot R[\Omega \cdot F] = 4.0 \times 10^{-4}$ is the same as that shown by the graph in FIG. 12.

Hence, when the above-mentioned configuration condition is satisfied, with the above-described simple configuration including the parallel-connected capacitor, a decay of 10 [dB] to 30 [dB] at 10 [kHz] and a decay of 30 [dB] to 50 [dB] at 100 [kHz] are achieved, and the high frequency environmental noise can be reduced in the output of the tunnel magnetoresistive elements.

Therefore, (i) the amplitude put on the connection conductive lines (Line-a and Line-b) greatly decreases, and a noise gradual decrease effect on electromagnetic coupling between the connection conductive lines (Line-a and Line-b) and the surroundings increases; (ii) gain of the amplifier circuit of the first stage placed after the connection conductive lines can be increased, and hence dynamic range increases and accuracy of signals in the preamplifier system increases; and (iii) the noise gradual decrease effect with the low-pass filter (LPF) increases.

That is, it is preferable that (i) each assembly 40 shown in FIG. 14 include: a tunnel magnetoresistive module including tunnel magnetoresistive elements which detect a biomagnetic signal; and a capacitor which temporarily receives the output from the tunnel magnetoresistive module and outputs the output to a circuit placed after the capacitor, (ii) the tunnel magnetoresistive module and the capacitor be mounted on the same substrate, and (iii) the condition of $4.0 \times 10^{-5} < C \cdot R[\Omega \cdot f] < 4.0 \times 10^{-4}$ be satisfied, wherein $R[\Omega]$ represents the resistance value of the tunnel magnetoresistive module with no magnetic field applied, and $C[F]$ represents the capacitance of the capacitor. By satisfying the condition of $4.0 \times 10^{-5} < C \cdot R[\Omega \cdot F] < 4.0 \times 10^{-4}$, high frequency signals exceeding the frequency band of biomagnetic signals are cut. Accordingly, there are effects as follows; the high frequency environmental noise component can be reduced in the output of the tunnel magnetoresistive elements, can be prevented from entering the amplifier circuit system at the entrance as much as possible, and can be separated from biomagnetic signals. In addition, the dynamic range can be widen and the detection performance can be improved.

Further, in order to amplify the detection signal of the TMR module 1, it is preferable that the resistance value of the fixed resistor Rc be 0.4R or more and 2.5R or less (R represents the resistance value of the TMR module 1 with no magnetic field applied). This is because the output V changes depending on the resistance value of the tunnel magnetoresistive elements 10, and as described in the above embodiment with reference to the graph shown in a of FIG. 13, when the resistance value of the fixed resistor Rc is 0.4R or more and 2.5R or less, the output difference ΔV is more than about 80% of the maximum value, and a very small change of the resistance value of the tunnel magnetoresistive (TMR) elements is conveyed with a large output difference ΔV.

Modifications from the embodiment are not limited to that shown in FIG. 14, and hence the circuit configurations shown in FIGS. 17 to 21 can demonstrate the same effects as those demonstrated by the circuit configuration shown in FIG. 14. In the circuit configurations shown in FIGS. 17 to 21, capacitors Ca1, Ca2, Ca3 and/or Ca4 are used, and an electrode 50 is grounded.

Figure 17:
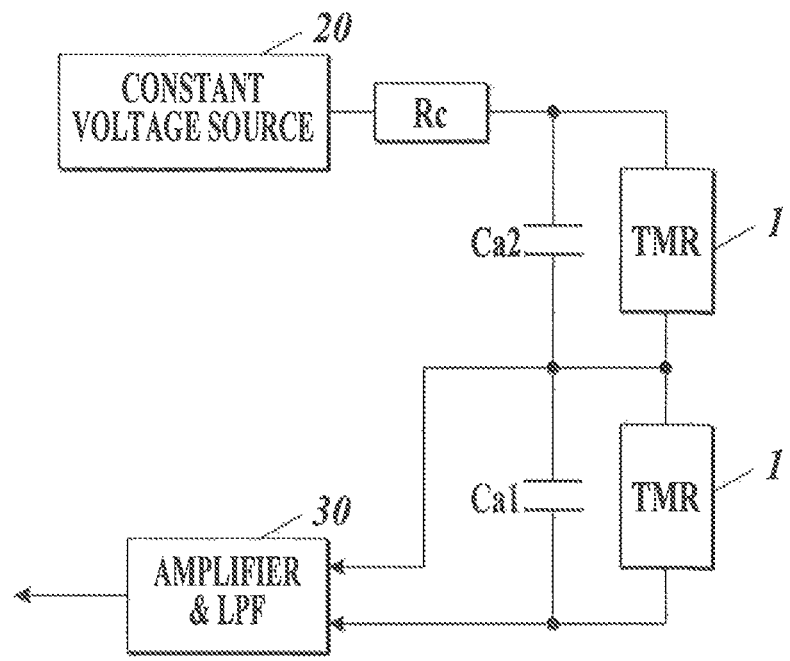
FIG. 17 is a block circuit diagram of an assembly according to another modification from the embodiment of the present invention.

As shown in FIG. 17, two sets, each set constituted of a TMR module 1 and a capacitor (Ca1 or Ca2), may be connected, and the TMR module 1 and the capacitor Ca2 which are connected to each other in parallel may be connected to between a connection line to a preamplifier unit 30 and a fixed resistor Rc, the connection line being arranged immediately before the TMR module 1 and the capacitor Ca1 of the second stage.

Figure 18:
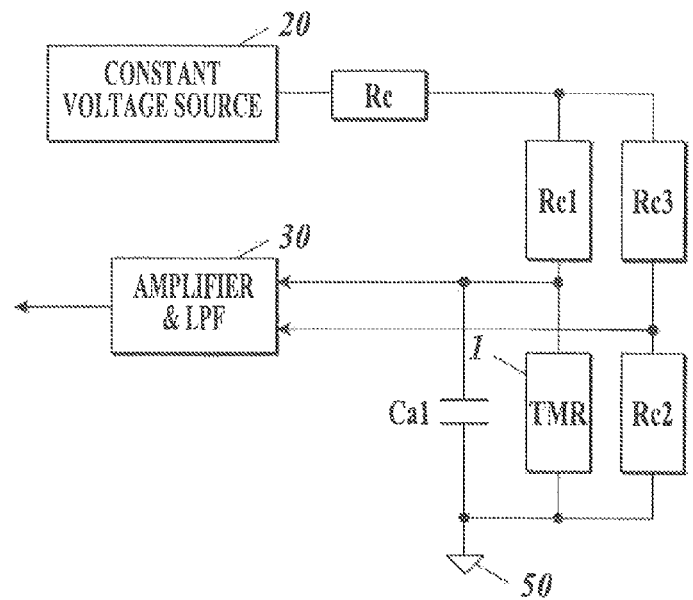
FIG. 18 is a block circuit diagram of an assembly according to another modification from the embodiment of the present invention.
Figure 19:
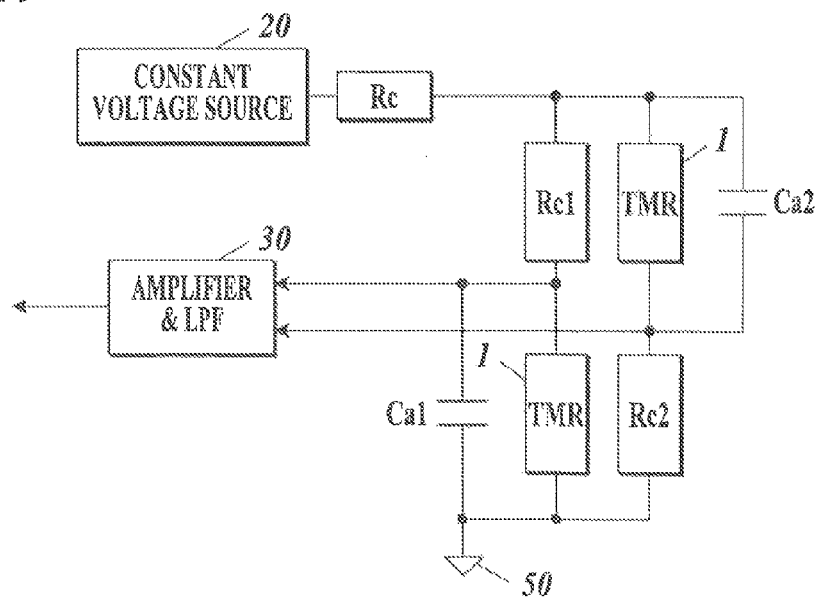
FIG. 19 is a block circuit diagram of an assembly according to another modification from the embodiment of the present invention.
Figure 20:
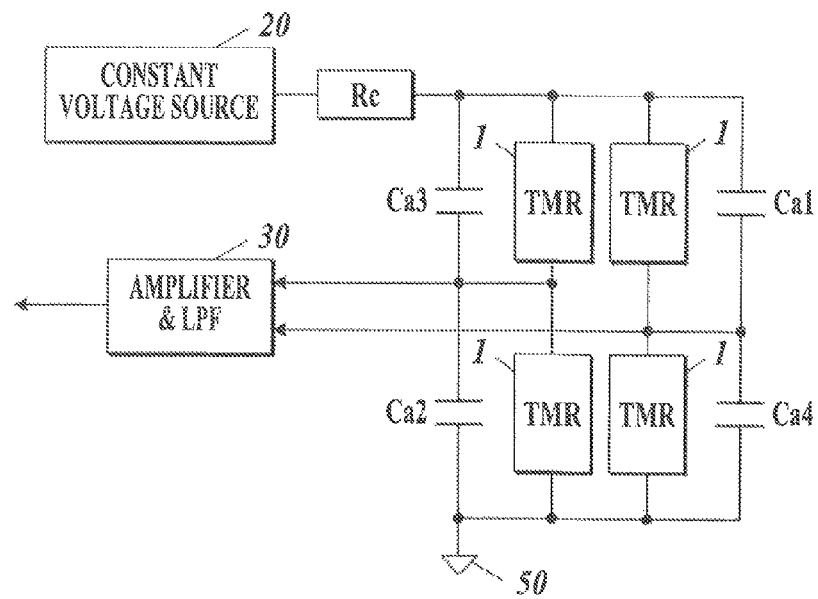
FIG. 20 is a block circuit diagram of an assembly according to another modification from the embodiment of the present invention.

As with the circuits shown in FIGS. 18 to 21, a differential amplifier circuit may be formed by arranging a plurality of TMR modules 1 (FIGS. 19 to 21) or by arranging a TSR module 1 and a resistor(s) (FIG. 18). In particular, the circuits shown in FIGS. 19 and 20 are each configured as a circuit like the Wheatstone bridge, and hence the change of a signal can be accurately detected with the simple circuit configuration. When a bridge is constituted of one TMR module 1 and three resistors Rc1 to Rc3 as shown in FIG. 18, the number of TMR modules 1 is small, so that there is an advantage, namely, the circuit can be easily formed.

Figure 21:
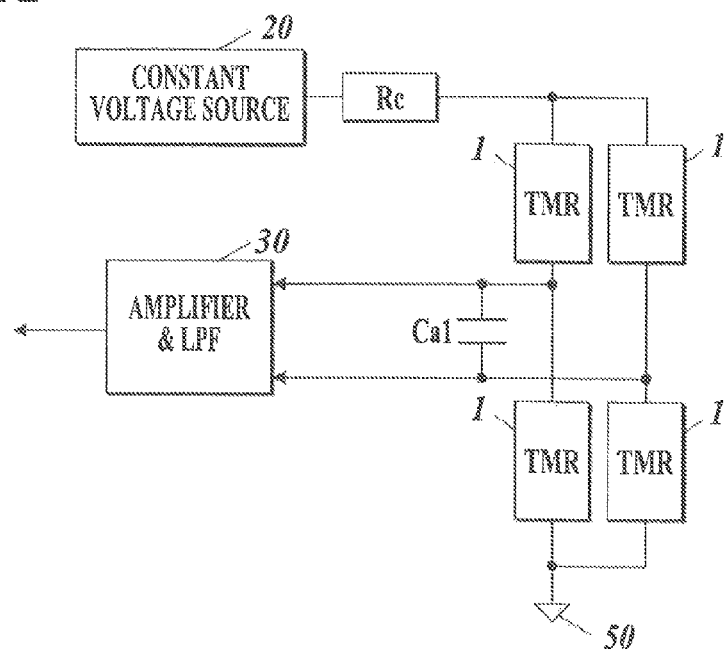
FIG. 21 is a block circuit diagram of an assembly according to another modification from the embodiment of the present invention.

In the circuit shown in FIG. 21, a bridge is constituted of four TMR modules 1, and a capacitor Ca1 is arranged to connect their intermediate points. With this circuit configuration too, the high frequency band environmental noise can be reduced in the outputs of the TMR modules 1 by the capacitor Ca1 before entering a preamplifier unit 30.

The entire disclosure of Japanese Patent Application No. 2011-113055 filed on May 20, 2011 and Japanese Patent Application No. 2011-123990 filed on Jun. 2, 2011, including the descriptions, claims, drawings and abstracts, is incorporated in the present application by reference in its entirety.

Industrial Applicability

There is usability as a magnetic sensor and a biomagnetism measurement system to measure biomagnetism in the medical field.

EXPLANATION OF REFERENCES

4 Assembly Unit
6 Fitting Unit
7 Holding Grid
10 Tunnel Magnetoresistive Element
11 Fixed Magnetic Layer
12 Free Magnetic layer
20 Capacitor
30 Fixed Resistor

The invention claimed is:

1. A magnetic sensor comprising a plurality of assemblies combined, each of the assemblies including a plurality of tunnel magnetoresistive elements each (i) including: a fixed magnetic layer having a fixed magnetization direction; a free magnetic layer having a changeable magnetization direction which changes by influence of a magnetic flux from outside; and an insulating layer disposed between the fixed magnetic layer and the free magnetic layer and (ii) changing a current flowing from the fixed magnetic layer to the free magnetic layer depending on an angular difference between the magnetization direction of the fixed magnetic layer and the magnetization direction of the free magnetic layer, wherein the assembly includes: the tunnel magnetoresistive elements (i) disposed in such a way that the magnetization directions of the fixed magnetic layers are substantially identical and the magnetization directions of the free magnetic layers with no magnetic field applied are substantially identical and (ii) connected to each other in series-parallel; a capacitor connected in parallel to the tunnel magnetoresistive elements which are connected to each other in series-parallel; and a fixed resistor connected in series to the tunnel magnetoresistive elements which are connected to each other in series-parallel and to the capacitor, and the assemblies are (i) disposed in such a way that the magnetization directions of the fixed magnetic layers of the assemblies have a relative angle of more than 90 degrees and (ii) connected to each other in series and/or in parallel.

2. The magnetic sensor according to claim 1, wherein the relative angle is substantially 180 degrees.

3. The magnetic sensor according to claim 1, wherein the assemblies are disposed at intervals of a predetermined space.

4. The magnetic sensor according to claim 1, wherein in the tunnel magnetoresistive element, the magnetization direction of the free magnetic layer with no magnetic field applied and the magnetization direction of the fixed magnetic layer are different from each other.

5. The magnetic sensor according to claim 1, wherein a resistance value of the fixed resistor of the assembly is 0.4R or more and 2.5R or less, wherein $R[\Omega]$ represents a resistance value of the tunnel magnetoresistive elements with no magnetic field applied, the tunnel magnetoresistive elements being connected in series to the fixed resistor in the assembly.

6. The magnetic sensor according to claim 1, wherein
the tunnel magnetoresistive elements and the capacitor are mounted on a same substrate, and
$4.0 \times 10^{-5} < C \cdot R[\Omega \cdot F] < 4.0 \times 10^{-4}$ is satisfied, wherein $R[\Omega]$ represents a resistance value of the tunnel magnetoresistive elements with no magnetic field applied, and $C[F]$ represents capacitance of the capacitor.

7. The magnetic sensor according to claim 1, wherein
the tunnel magnetoresistive elements and the fixed resistor are connected to a constant voltage source in series, and
an output line for a detection signal is taken out from between the tunnel magnetoresistive elements and the fixed resistor.

8. The magnetic sensor according to claim 6, wherein the substrate is any of a glass epoxy substrate, a polyimide substrate, a ceramic substrate and a glass substrate.

9. The magnetic sensor according to claim 6, wherein a wire on the substrate does not include a magnetic substance.

10. A biomagnetism measurement system comprising:
a plurality of magnetic sensors according to claim 1; and
an arithmetic device which generates biomagnetism information on the basis of a detection signal of the magnetic sensors.

* * * * *